United States Patent
Schultz et al.

(10) Patent No.: US 7,525,006 B2
(45) Date of Patent: *Apr. 28, 2009

(54) PROCESS FOR PRODUCING CUMENE

(75) Inventors: Michael A. Schultz, Des Plaines, IL (US); Steven P. Lankton, Des Plaines, IL (US); Constante P. Tagamolila, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/752,528

(22) Filed: May 23, 2007

(65) Prior Publication Data
US 2008/0293986 A1 Nov. 27, 2008

(51) Int. Cl.
C07C 15/073 (2006.01)
C07C 2/64 (2006.01)

(52) U.S. Cl. .................. 585/323; 585/450; 585/470

(58) Field of Classification Search ............ 585/323, 585/450, 470
See application file for complete search history.

(56) References Cited

U.S. PATENT DOCUMENTS

| 2,471,134 | A  | 5/1949  | Wright ............... 196/100 |
| 4,230,533 | A  | 10/1980 | Giroux ............... 203/1 |
| 5,902,917 | A  | 5/1999  | Collins et al. ......... 585/323 |
| 6,348,637 | B1 | 2/2002  | Harris ............... 585/820 |
| 6,395,950 | B1 | 5/2002  | Rice ................ 585/738 |
| 6,395,951 | B1 | 5/2002  | Hamm ............... 585/827 |
| 6,417,420 | B1 | 7/2002  | Stewart et al. ......... 585/323 |
| 6,479,720 | B1 | 11/2002 | O'Brien et al. ........ 585/448 |
| 6,483,002 | B1 | 11/2002 | O'Brien ............. 585/826 |
| 6,551,465 | B1 | 4/2003  | Van Zile et al. ....... 202/158 |
| 6,740,789 | B1 | 5/2004  | Bozzano et al. ....... 585/323 |
| 6,762,334 | B1 | 7/2004  | Stewart et al. ........ 585/323 |
| 6,927,314 | B1 | 8/2005  | Schultz et al. ........ 585/734 |

(Continued)

FOREIGN PATENT DOCUMENTS

EP    0 806 406 A1    11/1997

(Continued)

OTHER PUBLICATIONS

Schultz, Michael A. et al., "Reduce Costs with Dividing-Wall Columns" www.cepmagazine.org May 2002 pp. 64-71.

(Continued)

*Primary Examiner*—Thuan Dinh Dang
(74) *Attorney, Agent, or Firm*—Maryann Maas

(57) ABSTRACT

This cumene process involves contacting, in an alkylation zone, a first benzene recycle stream and a propylene feed stream with an alkylation catalyst to form cumene. In a transalkylation zone, a polyisopropyl benzene recycle stream and a second benzene recycle stream are contacted with a transalkylation catalyst to form additional cumene. The effluents are passed into a dividing wall distillation column. A cumene stream is removed from an intermediate point of the dividing wall fractionation column; a first benzene recycle stream is removed from a first end and a heavy aromatics stream is removed from a second end. A second benzene recycle stream is removed from an intermediate point located between the first end and the cumene stream. A polyisopropyl benzene stream is removed from an intermediate point of located between the second end and the cumene stream.

7 Claims, 1 Drawing Sheet

U.S. PATENT DOCUMENTS

| | | |
|---|---|---|
| 6,979,394 B2 | 12/2005 | Bozzano et al. ............... 208/12 |
| 7,060,852 B2 | 6/2006 | Maas et al. .................... 562/94 |
| 2001/0052453 A1* | 12/2001 | Rust et al. ................... 202/158 |
| 2002/0017480 A1 | 2/2002 | Emmrich et al. ............ 208/313 |
| 2002/0019576 A1 | 2/2002 | Emmrich et al. ............ 585/866 |
| 2004/0011706 A1 | 1/2004 | Kaibel et al. ................ 208/347 |
| 2004/0020757 A1 | 2/2004 | Deibele et al. ................ 203/21 |
| 2004/0254411 A1 | 12/2004 | Steinbrenner et al. ....... 585/323 |
| 2006/0052630 A1 | 3/2006 | Narbeshuber et al. ......... 562/81 |
| 2006/0101852 A1 | 5/2006 | Porter ......................... 62/620 |
| 2006/0178544 A1* | 8/2006 | Murray et al. .............. 585/467 |

FOREIGN PATENT DOCUMENTS

| | | |
|---|---|---|
| EP | 1 205 460 A1 | 5/2002 |
| WO | WO 03/051799 A1 | 6/2003 |

OTHER PUBLICATIONS

Rudd, Howard "Thermal coupling for energy efficiency" *Supplement to The Chemical Engineer* Aug. 27, 1992 pp. s14-s15.

Muralikrishna, K. et al., "Development of Dividing Wall Distillation Column Design Space for a Specified Separation" *Trans IChemE* vol. 80, Part A Mar. 2002 pp. 155-166.

* cited by examiner

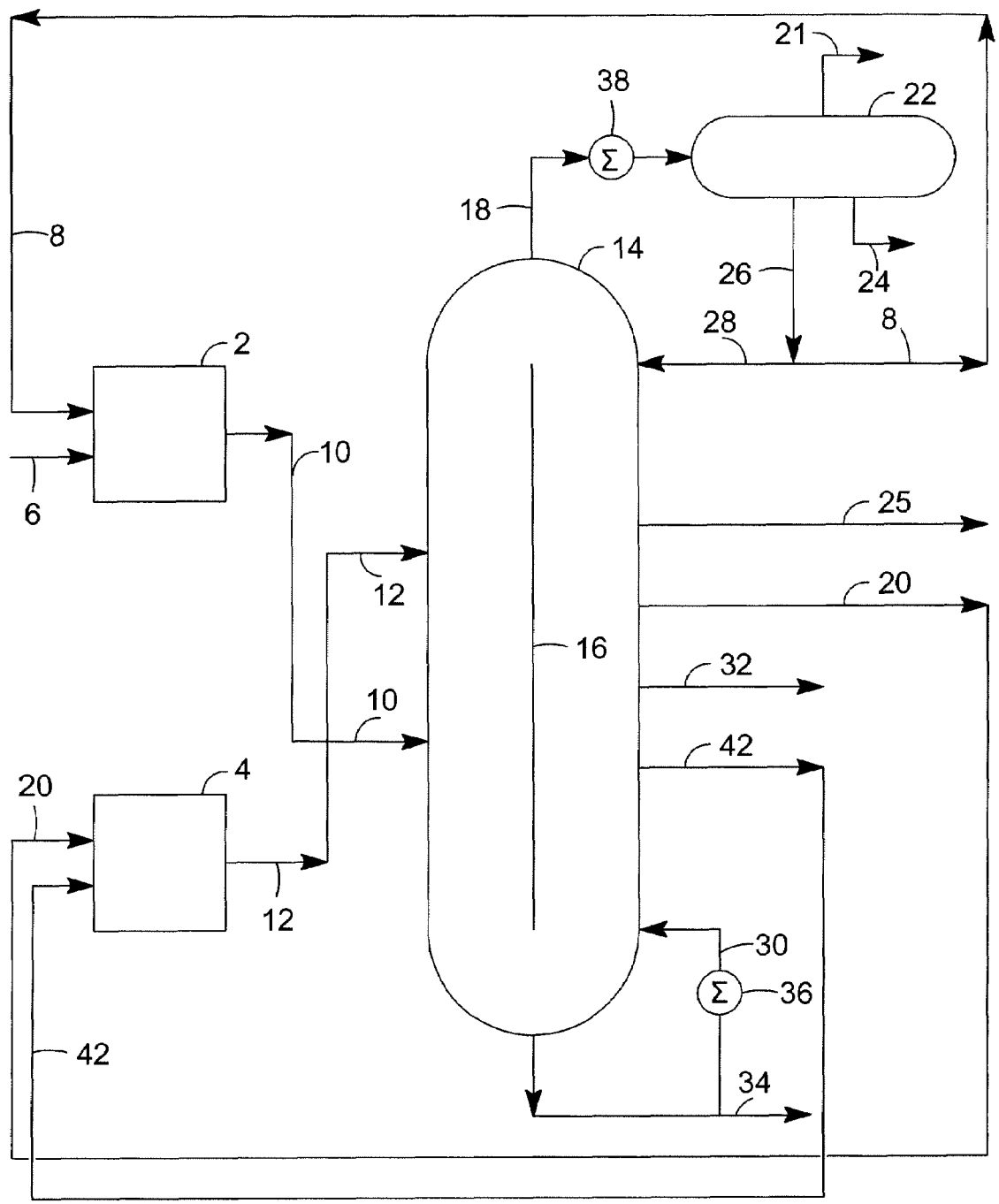

PROCESS FOR PRODUCING CUMENE

FIELD OF THE INVENTION

The invention is directed to a process for producing cumene where the product is separated from the reaction mixture using a dividing wall distillation column.

BACKGROUND OF THE INVENTION

Cumene, or isopropylbenzene, is a valuable product that is used mainly for the manufacture of phenol and acetone. Cumene has been produced by a catalytic process using a solid phosphoric acid that is made by impregnating kieselguhr with phosphoric acid. Now, zeolitic catalysts are used to produce higher quality cumene at a lower investment cost.

In a typical commercial process for the production of cumene, liquid benzene and liquid propylene are charged into an alkylation zone containing one or more reactors containing an alkylation catalyst. In order to minimize the production of dialkylated products of benzene it has been the practice to maintain a molar excess of benzene throughout the reaction zone ranging from about 4:1 to about 16:1, and more preferably about 8:1 of benzene to propylene. Two competing reactions with the desired production of isopropylbenzene have created problems in some commercial processes. One of these has been the formation of dialkylated benzenes such as di- and triisopropylbenzene rather than the desired monoalkylated product. This competing reaction may be partially controlled by employing large molar excesses of benzene. However, a transalkylation reactor is employed to react dialkylated benzenes with benzene to form additional cumene. The other competing reaction causing losses in the yield of cumene based on propylene reactant charged is the formation of oligomers of propylene such as propylene dimer and trimer which occur to a limited extent even with the large molar excesses of benzene present. Propylene trimers and some of the propylene tetramers boil with cumene. Since the presence of these olefins interfere with the oxidation reaction used to make phenol from cumene, this oligomerization side reaction must be minimized to make a high purity product.

The alkylator and transalkylator effluents undergo separation operations to separate benzene, cumene product, polyisopropylbenzene, and by-product streams using distillation columns. Traditionally three distillation columns are used. The first is typically a benzene column, used to recover excess benzene from the reactor effluents. The benzene column overhead, which is largely benzene, is typically recycled to the alkylator and transalkylator. The second distillation column is typically a cumene column used to recover the cumene product from the benzene column bottoms. The cumene product is typically the net overhead from the cumene column. The cumene product may be used in applications such as phenol or acetone processes, or may be sent to storage. The third distillation column is usually a polyisopropylbenzene column used to recover polyisopropylbenzene recycle stream from the cumene column bottoms. Polyisopropylbenzene is recovered as overhead from the polyisopropylbenzene column and is typically recycled to the transalkylator. The high boiling bottoms, the heavy ends, is usually cooled and sent to storage.

Current process flow schemes are improved by replacing the benzene column and the cumene column with a single dividing wall column. The resulting advantages include a significant savings in the energy requirement and the total number of stages, a higher cumene purity and a reduction in benzene loss. Additional advantages include a reduction in capital costs associated with the reduced number of stages, reduction in exchanger surface area, and a reduction in the equipment count.

The dividing wall or Petyluk configuration for fractionation columns was initially introduced some 50 years ago by Petyluk et al. A recent commercialization of a fractionation column employing this technique prompted more recent investigations as described in the article appearing at page s14 of a *Supplement to The Chemical Engineer*, 27 Aug. 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the claimed invention in the separation of aromatics comprising benzene, toluene and orthoxylene.

Using a dividing wall column in the a cumene production process provides significant advantages over cumene production processes that do not employ a dividing wall fractionation column, as shown below.

SUMMARY OF THE INVENTION

A cumene generation process having a dividing wall fractionation zone has been developed. The process involves contacting, in an alkylation zone, a feed stream comprising at least propylene and a first benzene recycle stream comprising at least benzene with an alkylation catalyst under alkylation conditions to convert at least a portion of the propylene and benzene into cumene and form an alkylation zone effluent comprising benzene and cumene. Also, in a transalkylation zone, a polyisopropyl benzene recycle stream comprising at least polyisopropyl benzene and a second benzene recycle stream comprising at least benzene are contacted with a transalkylation catalyst under transalkylation conditions to convert at least a portion of the polyisopropyl benzene and benzene into cumene and form a transalkylation zone effluent comprising benzene and cumene. The alkylation zone effluent and the transalkylation zone effluent are passed into a dividing wall fractionation column which is operated at fractionation conditions. The dividing wall fractionation column is divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column. The effluents from the two reactions zones enter the dividing wall column at one or more intermediate points of the first fractionation zone.

A stream comprising cumene, or isopropyl benzene, is removed from an intermediate point of the second fractionation zone of the dividing wall fractionation column. A first benzene recycle stream is removed from a first end of the dividing wall fractionation column, and a heavy aromatics stream is removed from a second end of the dividing wall fractionation column. The second benzene recycle stream is removed from an intermediate point of the second fractionation zone of the dividing wall fractionation column located between the first end of the column and intermediate point where the cumene stream is removed. A polyisopropyl benzene stream is removed from an intermediate point of the second fractionation zone of the dividing wall fractionation column located between the second end of the column and the intermediate point where the cumene stream is removed. Optionally a semi-dry benzene stream may be removed from an intermediate point of the second fractionation zone of the dividing wall fractionation column located between the first end of the column and the location where the second benzene recycle stream is removed from the dividing wall column.

BRIEF DESCRIPTION OF THE DRAWING

The FIGURE is a schematic illustration of one embodiment of the present invention. The FIGURE does not show a number of details for the process arrangement such as pumps, compressors, valves, stabilizers and recycle lines which are well known to those skilled in the art.

DETAILED DESCRIPTION OF THE INVENTION

Referring to the FIGURE, the process of the invention requires two reactors, an alkylation reactor 2, or alkylator, and a transalkylation reactor 4, or transalkylator. Propylene and benzene feedstocks 6 and an excess of benzene 8 are introduced to alkylator 2. A typical propylene feedstock may be an almost pure polymer grade material or can contain significant amounts of propane, as typically found in refinery-grade propylene. A typical benzene feedstock may contain benzene (99.9 wt.-% mm.) and toluene (0.05 wt.-% min). Alkylation reactors may be operated in the vapor phase, liquid-phase or mixed-phase. It is preferred to operate the alkylation reactor in the liquid phase. At the lower temperatures of the liquid phase operation, xylene impurities are not produced and a cumene product of superior quality is produced. Suitable temperatures include from about 100 to about 310° C. and from about 150 to about 280 ° C. Suitable pressures include from about 8 to 50 bar (gage) and from about 10 to 38 bar (gage). Alkylation reactor 2 contains an effective amount of alkylation catalyst. Suitably alkylation catalysts include solid acid catalysts and preferably a solid oxide zeolite. Examples are zeolite beta, zeolite X, zeolite Y, mordenite, faujasite, zeolite omega, UZM-8, MCM-22, MCM-36, MCM-49 and MCM-56. In one embodiment, the temperature of the alkylation reactor is selected from the range of 100° C. to 310° C. (212 to 590° F.) and the pressure is selected from the range of 800 to 5000 kPa (gauge) (116 to 725 psig). In a more specific embodiment the temperature is in the range of 120 to 280° C. (248 to 536° F.) and the pressure is in the range of from about 1000 to 3800 kPa (gauge) (145 to 551 psig). Alkylation reactors, operating conditions and catalysts are known in the art and not further discussed here.

In alkylation reactor 2, the benzene is alkylated with the propylene to form isopropylbenzene or cumene. Some polyisopropyl benzenes, which are mainly di- and tri-substituted propylbenzenes, are also formed. Benzene is fed to the alkylator in excess so that virtually all the propylene is reacted. The alkylation reactor effluent 10 contains primarily benzene, cumene and polyisopropyl benzenes.

Transalkylation reactor 4 is used to transalkylate the polyisopropyl benzene produced in the alkylation reactor and recycled in line 42 with benzene recycled in line 20 to form additional cumene. Suitable conditions and catalysts may be the same as described for the alkylation reactor. In one embodiment, the temperature is selected from the range of 100° C. to 270° C. (212 to 518° F.) and the pressure is selected from the range of 800 to 5100 kPa (116 to 740 psia). In another more specific embodiment, the temperature is about 129° C. (264° F.) and the pressure ranges from about 1000 to 3900 kPa (145 to 565 psig). Transalkylation reactors, operating conditions and catalysts are known in the art and not further discussed here. The transalkylation effluent 12 from transalkylation reactor 4 contains primarily benzene, cumene, and polyisopropyl benzene.

Both alkylation effluent 10 and transalkylation effluent 12 are introduced to a dividing wall distillation column 14. Within the dividing wall distillation column are two parallel fractionation zones. A first fractionation zone occupies a large portion of the left-hand side of the mid-section of the distillation column. Note that the terms "left-hand" and "right-hand" are used herein as relative to the drawings. In actual practice the placement of the zones as to the left side or the right side of the column is not critical. This first fractionation zone is separated from a parallel second fractionation zone occupying the other half of the column cross section by a substantially fluid tight vertical wall 16. The vertical wall is not necessarily centered in the column and the two fractionation zones may differ in cross sectional area or shape. The vertical wall divides a large vertical portion of the column into two parallel fractionation zones. The two zones are isolated from each other for the height of this wall, but communicate at both the top and bottom ends of the column. There is no direct vapor or liquid flow between the two fractionation zones through the dividing wall, but the upper end of the fractionation zone is open to the internal volume of the distillation column containing an undivided fractionation zone preferably having additional trays. Liquid may pass under the dividing wall at the bottom of the two fractionation sections although vapor flow is preferably restricted or controlled. Thus, vapor and liquid can freely move around the wall between the two portions of the column.

During operation, the components of both effluents are separated in the first fractionation zone with the more volatile compounds moving upward out of the left-hand first fractionation zone and emerging into the undivided upper portion of the distillation column. As with the first fractionation zone, the upper end of the right-hand second zone is in open communication with the upper section of the distillation column which may optionally contain additional fractionation trays extending across the entire column cross section.

The components of the effluents will separate according to boiling point or relative volatilities, which is the main factor in determining their behavior in the distillation column. The component having a relatively low boiling point is the benzene from each of the effluents. The mid-range boiling component is the desired product, cumene. The components having relatively higher boiling points are the polyisopropyl benzenes, and the components having the highest boiling points are any heavy aromatics.

The transalkylation effluent 12 and the alkylation effluent 10 are introduced into a first vertical fractionation zone occupying a large portion of the left-hand side of the midsection of the distillation column. The effluents may be combined before being introduced, but advantages may be realized by introducing the effluents at different heights along the dividing wall distillation column. For example, the alkylation reactor effluent may contain a higher concentration of polyisopropyl benzene and therefore it may be advantageous to introduce the alkylation reactor effluent at a relatively lower height along the column as compared to the transalkylation reactor effluent.

The benzene present in the effluents is driven upwards in the first fractionation zone and enters the top section of the column where it is removed in overhead 18 and sidedraw 20. Benzene in overhead 18 is removed from the top of the dividing wall column and passed through an overhead condenser 38 to form liquid delivered to receiver 22. Receiver 22 may also have vent stream 21. A liquid phase stream of benzene 26 is removed from the receiver and divided into a first portion 28 which is returned to the top of the dividing wall fractionation column as reflux and a second portion 8 which is recycled to the alkylation reactor 2 as the first benzene recycle stream. Benzene may also be removed from dividing wall column in stream 20 which is a sidedraw. Benzene stream 20 may be recycled to transalkylation reactor 4 as the second benzene recycle stream. As used herein the term "rich" is intended to indicate a concentration of the indicated compound or class of compounds greater than 50 and preferably greater than 75 mol percent.

The bottom of the dividing wall fractionation column 14 also comprises an undivided fractionation zone. This zone can receive liquid draining from both the first and second fractionation zones. This liquid is subjected to distillation which drives the cumene and polyisopropyl benzene upwards as vapor while concentrating the less volatile tars into a bottoms liquid 34 that is removed from dividing wall fractionation column 14. This separation is effected through the use of a reboiler 36 providing vapor to the bottom undivided fractionation zone. The product cumene stream 32 is withdrawn from the dividing wall fractionation column in a side draw from the right-hand side fractionation zone from the right-hand side fractionation zone. The byproduct polyisopropyl benzene stream 42 is withdrawn from the dividing wall fractionation column in a side draw. Polyisopropyl benzene stream 42 is withdrawn at a lower height of the column as compared to the cumene stream 32. A bottoms stream containing heavy aromatics is removed from the dividing wall distillation column and a portion of which is passed trough reboiler 36. The remainder is the net heavy aromatics stream 34.

Optionally, a semi dry benzene stream may be removed from the dividing wall fractionation column 14 in stream 25 as a side draw. Stream 25 is located at a height of dividing wall fractionation column between that of the first and second benzene recycle streams 8 and 20. Two benzene streams are withdrawn from the dividing wall fractionation column because the catalysts typically used in the alkylation reactor can tolerate some water present during the alkylation reaction, but the catalysts typically used in the transalkylation reactor are less tolerant of water. Therefore, the overhead contains benzene which may be saturated with water and is appropriate for the alkylation reactor, while the side draw contains semi-dry benzene which is appropriate for the transalkylation reactor.

The dividing wall fractionation column may be further equipped with stabbed-in reboilers and heat recovery exchangers located at strategic positions along the column. Examples of suitable locations for stabbed in reboilers include between the polyisopropyl benzene stream and the second end, and between the second benzene stream and the first end of the dividing wall distillation column. Such reboilers may be utilized to optimize the column diameter and energy consumption.

In a more specific embodiment of the invention, the undivided bottom section of the dividing wall fractionation column is depicted as separated from the two parallel fractionation zones by a gas flow control or gas trap out tray located just below the bottom of the wall. A slight gap at this point allows horizontal liquid flow between the parallel fractionation zones. This tray may have liquid sealed perforations allowing the normal downward flow of liquid, but its structure is such that the upward flow of vapor is at least greatly restricted or controlled. The tray may totally block the upward vapor flow. The use of this tray may provide a means to positively control the partition of the upward gas flow between the two fractionation zones, which is a prime means of controlling performance of the two zones. The total vapor from the column bottom, therefore, preferably removed from the column via a line and split between two lines which feed the vapor to the bottom of the two parallel fractionation zones separately. The gas flow may be controlled by one or more flow control valves or by adjusting the relative liquid levels in the bottom of the two zones. This is described in some detail in U.S. Pat. No. 4,230,533.

It is believed that the separation performed in the present invention would compare favorably to that achieved using a conventional scheme employing a benzene column followed by a cumene column and a polyisopropyl benzene column. An investigation would most likely indicate that the three conventional fractionation columns (the benzene column, the cumene column and the polyisopropyl benzene column) could be replaced with the dividing wall column of the present invention to provide significant benefits and costs savings. It is expected that the reboiling duty may decrease as well as the total number of required stages. Additionally, one might expect there to be a small increase in cumene recovery which translates into a smaller loss of cumene product. The total capital cost for the dividing wall column and its associated equipment, including heat exchangers, pumps, and receiving vessels, is expected to be less than the total for the columns it replaces, including the equipment associated with these columns. Several factors contribute to this cost reduction. First, as mentioned above, it is expected that the total reboiling duty may decrease as well as the total number of stages. The reduction in reboiling duty leads to a reduction in the size of the heat exchangers required for condensing and reboiling the column. In addition, the total pieces of equipment associated with a dividing fractionation wall column (including pumps, heat exchangers, and vessels) are fewer than the total required for the separate fractionation columns that it replaces. Fewer pieces of equipment for a more efficient separation will lead to a lower capital cost. The reduction in equipment count also leads to other less tangible benefits. The total plot space requirement for the separation is reduced. In addition, the total inventory of hydrocarbon is reduced, thereby providing, relatively, a more safe process unit.

The invention claimed is:

1. A cumene generation process using a dividing wall fractionation zone, said process comprising:
   contacting, in an alkylation zone, at least propylene and benzene and a first benzene recycle stream comprising at least benzene with an alkylation catalyst under alkylation conditions to convert at least a portion of the propylene and benzene into cumene and form an alkylation zone effluent comprising benzene and cumene;
   contacting, in a transalkylation zone, a polyisopropyl benzene recycle stream comprising at least polyisopropyl benzene and a second benzene recycle stream comprising at least benzene with a transalkylation catalyst under transalkylation conditions to convert at least a portion of the polyisopropyl benzene and benzene into cumene and form a transalkylation zone effluent comprising benzene and cumene;
   passing the alkylation zone effluent and the transalkylation zone effluent into a dividing wall fractionation column operated at fractionation conditions and divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the alkylation zone effluent and the transalkylation zone effluent entering the column at intermediate points of the first fractionation zone, wherein the transalkylation zone effluent is introduced into the dividing wall fractionation column at an intermediate height of the dividing wall fractionation column between the introduction point of the alkylation zone effluent and a first end of the dividing wall fractionation column;

removing a stream comprising cumene from an intermediate point of the second fractionation zone of the dividing wall fractionation column;

removing the first benzene recycle stream from the first end of the dividing wall fractionation column;

removing a heavy aromatic-rich stream from a second end of the dividing wall fractionation column;

removing the second benzene recycle stream from an intermediate point of the second fractionation zone of the dividing wall fractionation column located between the first end of the dividing wall fractionation column and the cumene stream; and removing a polyisopropyl benzene-rich stream from an intermediate point of the second fractionation zone of the dividing wall fractionation column located between the second end of the dividing wall fractionation column and the cumene stream.

2. The process of claim 1 wherein the alkylation zone is operated at a pressure in the range of 800 to 5100 kPa (116 to 740 psia) and a temperature in the range of 120 to 280° C. (248 to 536° F.).

3. The process of claim 1 wherein the transalkylation zone is operated at a pressure in the range of 800 to 5100 kPa (116 to 740 psia) and a temperature in the range of 100 to 200° C. (212 to 392° F.).

4. The process of claim 1 wherein the stream comprising cumene from the dividing wall fractionation column comprises 99.955 wt. % cumene.

5. The process of claim 1 wherein the stream comprising cumene from the dividing wall fractionation column comprises no more than about 4 wt. ppm benzene.

6. The process of claim 1 further comprising passing the stream comprising cumene to a phenol generation process.

7. The process of claim 1 further comprising passing the stream comprising cumene to an acetone generation process.

* * * * *